United States Patent [19]

Pitzele et al.

[11] Patent Number: 4,579,951

[45] Date of Patent: Apr. 1, 1986

[54] SUBSTITUTED (AZACYCLOALK-2-YL)IMINOPHENOLS AND ESTERS THEREOF

[75] Inventors: Barnett S. Pitzele, Skokie; Stella S. T. Yu, Morton Grove; Robert W. Hamilton, Wilmette, all of Ill.

[73] Assignee: G. D. Searle & Co., Skokie, Ill.

[21] Appl. No.: 590,663

[22] Filed: Mar. 19, 1984

[51] Int. Cl.$^4$ .................. C07D 211/56; C07D 207/14
[52] U.S. Cl. .................... 546/223; 546/194; 546/208; 546/212; 546/214; 548/517; 548/518; 548/527; 548/559
[58] Field of Search ......................... 548/559; 546/223

[56] References Cited

U.S. PATENT DOCUMENTS

| | | | |
|---|---|---|---|
| 3,563,994 | 2/1971 | Wollweber et al. | 546/223 |
| 3,769,274 | 10/1973 | Wollweber et al. | 548/559 |
| 3,887,569 | 6/1975 | Poos | 548/559 X |
| 4,468,403 | 8/1984 | Knaus et al. | 546/223 X |
| 4,533,739 | 8/1985 | Pitzele et al. | 548/559 |

OTHER PUBLICATIONS

H. J. Binder, "Net Fluid and Electrolyte Secretion: The Pathopysiologic Basis For Diarrhea," In *Mechanisms of Intestinal Secretion*, Ed. Alan R. Liss: New York, 1979, pp. 1–14.

H. I. Jacoby and C. H. Marshall, Antagonism of Cholera Enterotoxin by Anti-Inflammatory Agents in the Rat. *Nature*, 235, 163–165 (1972).

R. A. Fischer, "Principles of Statistical Estimation," In *Statistical Methods For Research Workers*, 14th. ed. Hafner: New York; pp. 301–339.

*Primary Examiner*—Joseph Paul Brust
*Attorney, Agent, or Firm*—Steven M. Odre; Stuart L. Melton

[57] ABSTRACT

This invention relates to novel substituted (azacycloalk-2-yl)iminophenols that are useful in the treatment of diarrhea.

30 Claims, No Drawings

SUBSTITUTED (AZACYCLOALK-2-YL)IMINOPHENOLS AND ESTERS THEREOF

BACKGROUND OF THE INVENTION (a) Field of the Invention

This invention relates to novel substituted (azacycloalk-2-yl)iminophenols of Formula I that are useful in the treatment of diarrhea.

Diarrhea is a condition characterized by an abnormally frequent discharge of liquid or semi-liquid from the bowel. The normal intestinal discharge occurs at variable intervals but usually not more than twice in twenty-four hours and typically has a semi-solid consistency. When a more liquid stool must be discharged more than three times a day, diarrhea exists. Diarrhea may have any of several causes. For example, eating indigestible or irritating foods or foods to which an individual is allergic may cause diarrhea. Too much roughage, such as found in bran, cabbage, or other fibrous foods often consumed to relieve constipation, may also induce diarrhea. Infection or nervousness, which can cause discharge before the intestinal contents can assume a normal form, are causes of diarrhea. Moreover, many drugs, particularly antibiotics, are known to cause diarrhea as a side effect.

Mild diarrhea has been treated with binding agents such as aluminum hydroxide gel, kaolin, pectin, and bismuth. More serious diarrhea has been treated with opiates, which act through a spasmogenic effect that inhibits propulsive activity in the intestine. Diphenoxylate (a synthetic opiate derivative), tincture of opium, and camphorated tincture of opium (paregoric) have all been used effectively for serious diarrhea. The compounds, however, treat symptoms rather than causes and have all the problems associated with opiates, such as addictive liability, mental confusion or discomfort, respiratory depression, nausea, and the like. Thus, care must be taken to avoid complications and even death.

(b) Prior Art

Certain phenyl-substituted cyclic amidines are known, but differ significantly from compounds of the present invention. U.S. Pat. No. 3,769,274 and U.S. Ser. No. 06/433,922, now U.S. Pat. No. 4,533,739, issued Aug. 6, 1985, the latter having the same assignee as this application, include compounds having amino or substituted-amino groups but do not disclose hydroxy or acyloxy groups on the phenyl nucleus. Only '922 discloses and claims antidiarrheal activity for these previously disclosed compounds.

U.S. Pat. No. 3,563,994 discloses compounds in which the phenyl substituents include, inter alia, alkoxy, alkanoyl (i.e., ketone compounds), or alkoxycarbonyl (i.e., benzoate ester compounds). In addition, the '994 patent discloses only antihypertensive activity, CNS damping effects, and inhibition of gastric acid (as opposed to intestinal fluid) secretion. The '994 patent, however, does not claim nor disclose compounds of this invention, in which phenyl substituents include hydroxy or acyloxy (i.e., phenolic ester compounds). Moreover, selected compounds encompassed within the '994 patent—two methoxy-substituted and one methoxycarbonyl-substituted analog—were found to be inactive or only weakly active in antisecretory antidiarrheal assays in which the compounds of this invention were, in sharp contrast, quite active.

SUMMARY OF THE INVENTION

The following compounds have been discovered to be useful as antidiarrheals which act by decreasing aqueous secretion in the intestines. Since the compounds do not exhibit the problems associated with opiates and since they act at the source of the condition rather than on the symptoms, the associated complications inherent in opiates may be eliminated.

The invention relates to compounds of Formula I:

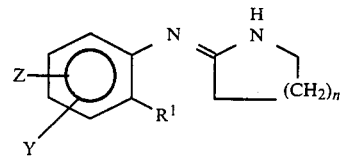

wherein Y is OR$^2$;
wherein Z is:
 (a) hydrogen;
 (b) alkyl of 1 to 6 carbon atoms, inclusive; or
 (c) halogen;
wherein R$^1$ is:
 (a) hydrogen;
 (b) alkyl of 1 to 6 carbon atoms, inclusive; or
 (c) halogen;
wherein R$^2$ is:
 (a) hydrogen; or
 (b) C(=O)R$^3$;
wherein R$^3$ is:
 (a) alkyl of 1 to 6 carbon atoms inclusive;
 (b) cycloalkyl of 3 to 8 carbon atoms, inclusive; or
 (c) multicyclic alkyl of 6 to 12 carbon atoms, inclusive, optionally substituted with one or more alkyl, each of 1 to 6 carbon atoms, inclusive;
 (d)

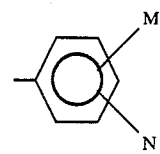

(e) heteroaryl of 5 or 6 nuclear ring atoms;
wherein M and N, each being the same or different, are:
 (a) hydrogen;
 (b) alkyl of 1 to 6 carbon atoms, inclusive;
 (c) alkoxy of 1 to 6 carbon atoms, inclusive; or
 (d) halogen;
wherein n is 1 or 2; and the pharmaceutically acceptable salts.

Although Formula I indicates one tautomeric form for the cyclic amidine moiety, it is understood that this representation is for convenience only and that the scope of this invention includes as equivalents all tautomeric forms of the compounds described herein.

Examples of alkyl of 1 to 6 carbon atoms, inclusive, are methyl, ethyl, propyl, butyl, pentyl, hexyl, and the isomeric forms thereof, generally referred to as alkyl.

Examples of cycloalkyl of 3 to 8 carbon atoms, inclusive, are cyclopropyl, cyclobutyl, cyclopentyl, cyclohexyl, cycloheptyl, and cyclooctyl.

Examples of multicyclic alkyl of 6 to 12 carbon atoms, inclusive, are bicyclo[2.1.1]hexane, bicyclo[2.2.1]heptane, bicyclo[2.2.2]octane, 1-adamantyl, and 2-adamantyl.

Examples of alkoxy of 1 to 6 carbon atoms, inclusive, are methoxy, ethoxy, propoxy, butoxy, pentoxy, hexoxy, and the isomeric forms thereof.

Examples of heteroaryl of 5 or 6 nuclear ring atoms include 2-thienyl, 2-furyl, 3-furyl, 2-pyrrolyl, 3-pyrrolyl, 2-pyridyl, 3-pyridyl, and 4-pyridyl.

Examples of halogen are fluorine, chlorine, bromine, and iodine.

Examples of pharmacologically acceptable acid addition salts include the hydrochloride, hydrobromide, hydroiodide, sulfate, phosphate, acetate, propionate, lactate, maleate, malate, succinate, and tartrate salts.

DESCRIPTION OF THE INVENTION

The compounds of this invention are prepared by methods illustrated in the following Scheme.

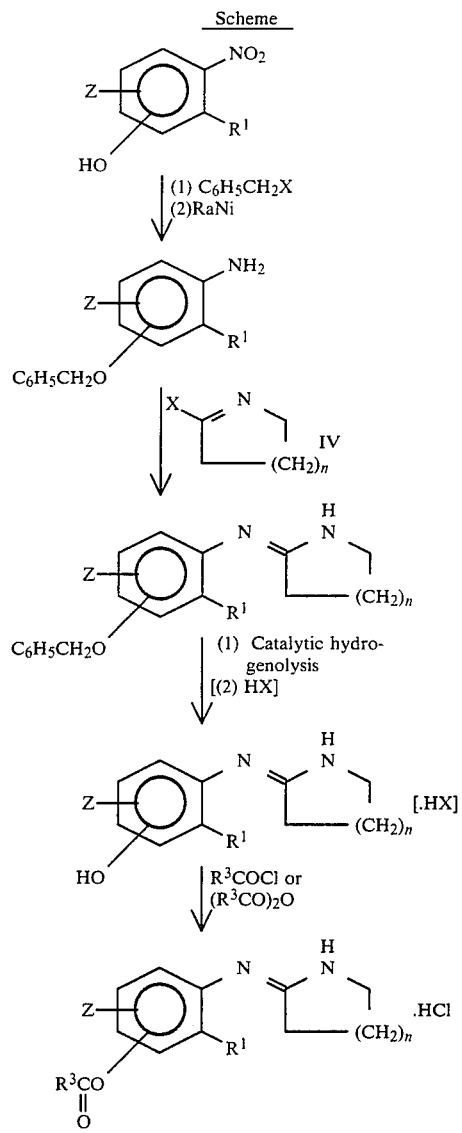

Substituted nitrophenols of Formula II are converted to corresponding O-protected anilines of formula III by any number of methods known in the art. A preferred method involves O-benzylation using a benzyl halide in the presence of an unreactive base, followed by reduction of the nitro intermediates to the corresponding anilines. Preferred benzylation conditions include reaction of a phenol, Formula II, with benzyl bromide in dimethylformamide in the presence of potassium carbonate. Preferred reduction conditions include hydrogenation of the O-protected intermediate with Raney nickel in tetrahydrofuran. Anilines of Formula III react with 2-haloazacycloalk-1-enes, Formula IV, to form O-benzylated (azacycloalk-2-yl)iminophenols of Formula V. Preferred conditions include adding an aniline of Formula III to an acetonitrile solution of freshly prepared 2-chloroazacycloalk-1-ene, followed by heating at reflux. The phenol compounds of this invention, Formula VI, are prepared by hydrogenolysis of benzyl ethers, Formula V. Acid addition salts may be prepared from amidine compounds of Formula VI during hydrogenolysis by including the appropriate acid or after hydrogenolysis by acid addition methods known to those in the art. A preferred hydrogenolysis method includes a methanolic (or methanol-tetrahydrofuran) solution of a benzyl ether under hydrogen gas with palladium on carbon as catalyst.

An alternative, but less preferred method for preparing phenols of Formula VI omits O-benzylation of nitrophenols of Formula II before reduction to corresponding anilines. Subsequent reaction with compounds of Formula IV affords the compounds of Formula VI.

Phenols of Formula VI react with an acyl halide or anhydride to afford phenolic esters of this invention, Formula VII. Preferred acylating conditions include heating (for example, in the range of 80° to 200°) a mixture of a phenol and an acid chloride (or acid anhydride where necessary) in the presence of titanium tetrachloride. Where acid addition salts other than hydrochlorides are desired, anion exchange methods known to those in the art may be employed.

The preferred embodiments of this invention include compounds of the following general structure, Formula VIII.

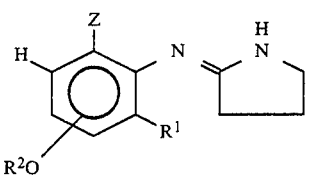

More specifically, the preferred embodiments include compounds of Formula VIII wherein $R^1$ is lower alkyl (that is, consisting of 1 to 6 carbon atoms, inclusive) or halogen; wherein Z is hydrogen, lower alkyl, or halogen; wherein $R^2$ is hydrogen or $C(=O)R^3$; and wherein $R^3$ is lower alkyl, cycloalkyl, or optionally substituted phenyl.

The most preferred embodiments of this invention include compounds of the following general structure, Formula IX.

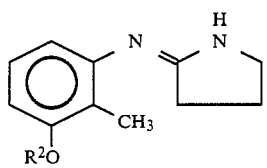

More specifically, the most preferred embodiments include compounds of Formula IX wherein $R^2$ is hydrogen or $C(=O)R^3$; and wherein $R^3$ is lower alkyl, cycloalkyl, or optionally substituted phenyl.

The antidiarrheal activity of the compounds of this invention illustrated in the examples was demonstrated by the following method. Lidamidine, a previously reported antisecretory antidiarrheal agent, is active in this assay.

CHOLERA-INDUCED INTESTINAL FLUID SECRETION

Excessive fluid secretion into the intestinal lumen is a major component of diarrhea (1). In order to determine the effect of the test compounds on intestinal fluid movements, the rat cholera model was used (2). Female Charles River rats weighing 85–100 g and having free access to water were fasted for 24 hours prior to each experiment. After a midline incision was made under ether anesthesia, a 20-cm ligated small intestinal segment was constructed starting 3.0 cm distal to the ligament of Treitz. Each segment was injected, using a 27 gauge ½-inch needle, with crude cholera toxin in a 0.9% saline solution. Thirty minutes before cholera toxin was injected, test compounds were administered subcutaneously to groups of four rats at doses of 10 and 20 mg/kg. Four hours after injection of toxin, the animals were sacrificed and the fluid content and exact length of the intestinal segments were measured. Fluid secretion was expressed in ml/cm of intestine.

The $ID_{50}$'s of these compounds were estimated using data obtained from at least two doses and at least two experiments by the method of maximum likelihood (3). Lower and upper limit values for the $ID_{50}$, between which the likelihood was more than one-twentieth of its maximum, were used to define an interval of estimation, approximating a 95% confidence interval. The routine calculation did not include a test of the slope of the dose-response curve.

See (1) H. J. Binder. "Net Fluid and Electrolyte Secretion: The Pathophysiologic Basis for Diarrhea." In *Mechanisms of Intestinal Secretion*. H. J. Binder, Ed. Alan R. Liss: New York, 1979; pp. 1–16; (2) H. I. Jacoby and C. H. Marshall. Antagonism of Cholera Enterotoxin by Anti-inflammatory Agents in the Rat. *Nature*, 235, 163–165 (1972); and (3) R. A. Fischer. "Principles of Statistical Estimation." In *Statistical Methods for Research Workers*, 14th ed. Hafner: New York; pp. 301–339.

By virtue of the antidiarrheal activity, the compounds of Formula I are useful in treating diarrhea in mammals. A physician or veterinarian of ordinary skill could readily determine whether a subject exhibits diarrhea. Regardless of the route of administration selected, the compounds of the present invention are formulated into pharmaceutically acceptable dosage forms by conventional methods known to those skilled in the art. The compounds may be formulated using pharmacologically acceptable acid addition salts. Morever, the compounds or their salts may be used in a suitable hydrated form.

Compounds of this invention also have useful analgesic properties as determined by standardized tests.

The compounds can be administered in such oral dosage forms as tablets, capsules, pills, powders, or granules. They may also be administered intraperitoneally, subcutaneously, intravascularly, or intramuscularly, using forms known to the pharmaceutical art. In general, the preferred form of administration is oral. An effective but non-toxic quantity of the compound is employed in treatment. the dosage regimen for preventing or treating diarrhea with the compounds of this invention is selected in accordance with a variety of factors, including the type, age, weight, sex, and medical condition of the patient; the severity of the diarrhea; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 0.1 to 1.0 mg/kg up to about 50 mg/kg orally.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees celsius unless otherwise noted.

DESCRIPTION OF THE PREFERRED EMBODIMENTS

Example 1

3-(phenylmethoxy)-2-methylaniline

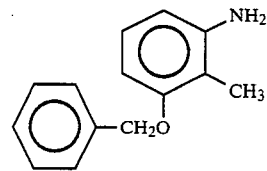

A mixture of 100 g of 2-methyl-3-nitrophenol, 113 g of benzyl bromide, and 100 g of potassium carbonate in 500 ml of dimethylformamide was stirred for three days at room temperature and then poured into 1500 ml of water. A solid was collected, washed with 5% aqueous sodium hydroxide and then water, and recrystallized from methanol, giving 156 g of the O-benzyl ether intermediate. Structure assignment of the intermediate was supported by the nmr spectrum (CDCl$_3$): δ (ppm) 2.40 (s, 3H, phenyl CH$_3$); 5.10 (s, 2H, benzyl CH$_2$); 6.9–7.6 (m's, 8H, aromatic CH's). A portion of the intermediate (30 g) in tetrahydrofuran was reduced in three hours using 4 psi of hydrogen and ca. 6.0 g of Raney nickel. The resultant title compound (27 g) was used in subsequent reactions without further characterization.

Example 2

3,4-dihydro-N-[2-methyl-4(phenylmethoxy)-phenyl]-2H-pyrrol-5-amine hydrochloride ⅛ hydrate

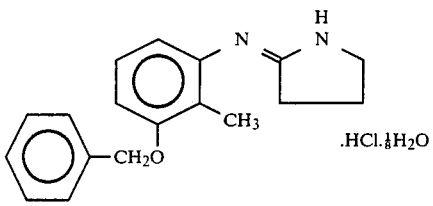

To a solution of 101 g of 2-pyrrolidinone in 1500 ml of acetonitrile cooled in an ice-methanol bath was added dropwise a solution of 91.3 g of phosphorus oxychloride in 30 ml of acetonitrile. After the reaction was stirred at room temperature for three hours, 127 g of the title product of Example 1 was added and the mixture heated at reflux for three hours. The mixture was concentrated in vacuo to a residue that was dissolved in hot water and filtered. The filtrate was washed with ethyl acetate and then made basic with 4N sodium hydroxide. Crude product was extracted into dichloromethane, which was removed in vacuo, and then purified by chromatography to give 118 g of the free base of the title compound. A portion (4 g) of the free base was converted to the hydrochloride salt (the title compound) by adding hydrogen chloride in isopropyl alcohol, followed by trituration with diethyl ether. Structure assignment was supported by the nmr spectrum and by elemental analysis.

nmr ((CD$_3$)$_2$SO): δ (ppm) 2.1 (m's, 5H, phenyl CH$_3$ and pyrrolidine CH$_2$); 3.08 and 3.58 (pair of m's, each 2H, pyrrolidine CH$_2$'s); 5.18 (s, 2H, benzyl CH$_2$).

Analysis Calcd. for C$_{18}$H$_{20}$N$_2$O.HCl.⅛H$_2$O: C, 67.75; H, 6.71; N, 8.78; Cl, 11.11. Found: C, 67.51; H, 6.51; N, 8.90; Cl, 11.21.

Example 3

3-[(3,4-dihydro-2H-pyrrol-5-yl)amino]-2-methylphenol hydrochloride, Method A

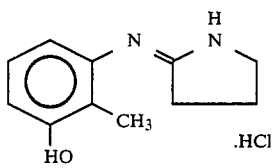

The title product of Example 2 (33 g) in ethanol containing 12 ml of concentrated hydrochloric acid was hydrogenolyzed at room temperature using 5 psi of hydrogen gas and 5 g of 5% palladium on carbon as catalyst. After three hours the catalyst was removed by filtration and the filtrate was concentrated to dryness, giving 24 g of the title compound. Structure assignment was supported by the nmr spectrum and by elemental analysis.

nmr ((CD$_3$)$_2$SO): δ (ppm) 2.02 (s, 3H, phenyl CH$_3$); 2.20, 3.10 and 3.55 (m's, each 2H, pyrrolidine CH$_2$'s).

Analysis Calcd. for C$_{11}$H$_{14}$N$_2$O.HCl: C, 58.28; H, 6.67; N, 12.36; Cl, 15.64. Found: C, 58.00; H, 6.69; N, 12.39; Cl, 15.27.

Example 4

3-[(3,4-dihydro-2H-pyrrol-5-yl)amino]-2-methylphenol hydrochloride, Method B

2-Methyl-3-nitrophenol (70 g) in 100 ml of tetrahydrofuran and 400 ml of methanol at room temperature was hydrogenated under 5 psi of hydrogen gas using 3.5 g of 5% palladium on carbon as catalyst. After removal of catalyst by filtration, the filtrate was concentrated to give 56 g of analytically pure 3-amino-2-methylphenol. This aminophenol was then converted to the title compound (7.9 g) using the general method of Example 2, except that the hydrochloride salt was formed by adding hydrogen chloride/dioxane to a methanol solution of the free base. The nmr spectrum and elemental analysis were in agreement with those of title compound prepared by Example 3 (Method A).

Example 5

3-[3,4-dihydro-2H-pyrrol-5-yl)amino]phenol hydrochloride

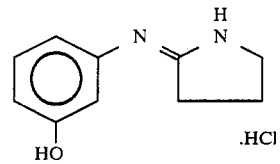

The title compound, m.p. 180°–187°, was prepared from 20 g of m-nitrophenol using the methods of Examples 1 (except that the initial benzyl intermediate was isolated by partitioning between water and dichloromethane, the latter containing the intermediate), 2, and 3 (except that the hydrogenation solvent was tetrahydrofuran-methanol and the title compound was induced to crystallize with methanol and diethyl ether). Structure assignment was supported by the nmr spectrum and by elemental analysis.

nmr ((CD$_3$)$_2$SO): δ (ppm) 2.10, 3.10 and 3.55 (m's, each 2H, pyrrolidine CH$_2$'s); 6.5–7.5 (m's, 4H, phenyl CH's).

Analysis Calcd. for C$_{10}$H$_{12}$N$_2$O.HCl: C, 56.47; H, 6.16; N, 13.17; Cl, 16.67. Found: C, 56.07; H, 6.11; N, 13.06; Cl, 16.67.

Example 6

4-[(3,4-dihydro-2H-pyrrol-5-yl)amino]-3-methylphenol ¼ hydrate

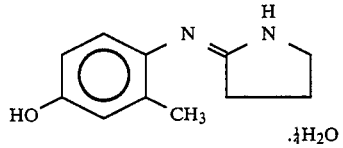

The title compound was prepared from 31 g of 3-methyl-4-nitrophenol using the methods of Examples 1, 2 (except that the chromatographically purified intermediate was not converted to the hydrochloride salt), and 3 (except that the hydrogenation solvent contained no hydrochloric acid). Structure assignment was supported by the nmr spectrum and by elemental analysis.

nmr ((CD$_3$)$_2$SO): δ (ppm 2.01 (s, 3H, phenyl CH$_3$); 2.01, 2.35 and 3.30 (m's, each 2H, pyrrolidine CH$_2$'s)

Analysis Calcd. for $C_{11}H_{14}N_2O.\frac{1}{4}H_2O$: C, 68.64; H, 7.59; N, 14.55. Found: C, 68.42; H, 7.42; N, 14.14.

Example 7

2-[(3,4-dihydro-2H-pyrrol-5-yl)amino]-3-methylphenol hydrochloride ⅜ hydrate

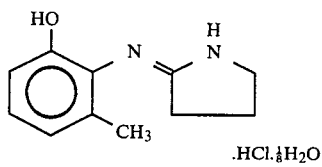

The title compound was prepared from 10 g of 3-methyl-2-nitrophenol using the methods of Examples 1, 2, and 3. Structure assignment was supported by the nmr spectrum and by elemental analysis.

nmr (($CD_3$)$_2$SO): δ (ppm) 2.18 (s, 3H, phenyl $CH_3$); 2.10, 3.08 and 3.54 (m's, each 2H, pyrrolidone $CH_2$'s).

Analysis Calcd. for $C_{11}H_{14}N_2O.HCl.\frac{3}{8}H_2O$: C, 57.71; H, 6.71; N, 12.23; Cl, 15.48. Found: C, 57.54; H, 6.52; N, 12.22; Cl, 15.63.

Example 8

3-[(3,4,5,6-tetrahydro-2-pyridin-5-yl)-amino]-2-methylphenol hydrochloride

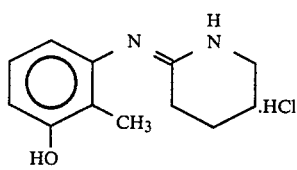

The title compound was prepared in the same manner as the title compound of Example 3 except that valerolactam was used instead of 2-pyrrolidinone (See Example 2) and the final hydrogenation solvent was tetrahydrofuran-methanol. Structure assignment was supported by the nmr spectrum and by elemental analysis.

nmr (($CD_3$)$_2$SO): δ (ppm) 1.74 (m, 4H, tetrahydropyridine $CH_2$'s); 1.98 (s, 3H, phenyl $CH_3$); 2.83 and 3.20 (m's, each 2H, tetrahydropyridine $CH_2$'s).

Analysis Calcd. for $C_{12}H_{16}N_2O.HCl$: C, 60.07; H, 7.14; N, 11.68; Cl, 14.78. Found: C, 59.74; H, 7.05; N, 11.63; Cl, 14.42.

Example 9

3-[(3,4-dihydro-2H-pyrrol-5-yl)amino]-2-chlorophenol hydrochloride

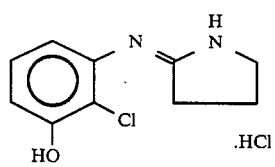

The title compound is prepared by the methods described in Example 4 using 2-chloro-3-nitrophenol.

Example 10

3-[(3,4-dihydro-2H-pyrrol-5-yl)amino]-2-methylphenyl 2,2-dimethylpropanoate hydrochloride ¼ hydrate

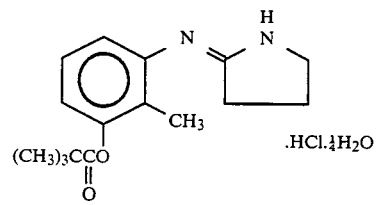

A mixture of 0.75 g of the title product of Example 3 and 10 ml of pivalic anhydride was stirred at 150° for about 4.5 hours. Upon cooling, the mixture was poured into diethyl ether. The resultant solid was collected by filtation, washed with diethyl ether, and dissolved in methanol. The solution was acidified with hydrogen chloride in isopropyl alcohol and crystallization induced by adding diethyl ether, giving the title compound. Structure assignment was supported by the nmr spectrum and by elemental analysis.

nmr (($CD_3$)$_2$SO): δ (ppm) 1.33 (s, 9H, pivalate $CH_3$'s); 2.04 (s, 3H, phenyl $CH_3$); 2.12, 3.07 and 3.54 (m's, each 2H, pyrrolidine $CH_2$'s); 7.0–7.5 (m's, 3H, phenyl CH's).

Analysis Calcd. for $C_{16}H_{22}N_2O_2.HCl.\frac{1}{4}H_2O$: C, 60.94; H, 7.51; N, 8.88; Cl, 11.24. Found: C, 61.14; H, 7.37; N, 8.62; Cl, 10.95.

Example 11

4-[(3,4-dihydro-2H-pyrrol-5-yl)amino]-3-methylphenyl 2,2-dimethylpropanoate hydrochloride

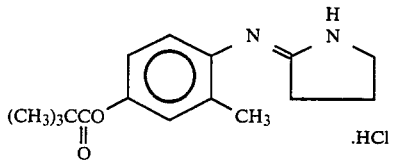

The title compound was prepared by the method of Example 10 using 0.5 g of the title product of Example 6. Structure assignment was supported by the nmr spectrum and by elemental analysis.

nmr (($CD_3$)$_2$SO): δ (ppm) 1.30 (s, 9H, pivalate $CH_3$'s); 2.23 (s, 3H, phenyl $CH_3$); 2.15, 3.03 and 3.57 (m's, each 2H, pyrrolidine $CH_2$'s).

Analysis Calcd. for $C_{16}H_{22}N_2O_2.HCl$: C, 61.83; H, 7.46; N, 9.01; Cl, 11.40. Found: C, 61.60; H, 7.27; N, 9.15; Cl, 11.60.

Example 12

3-[(3,4-dihydro-2H-pyrrol-5-yl)amino]-2-methylphenyl benzoate hydrobromide ¼ hydrate

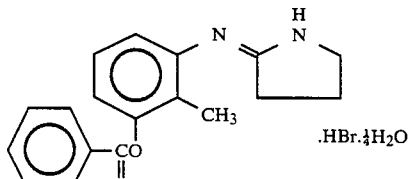

The title compound was prepared from 8.0 g of the title product of Example 3 using the general method described in Example 10, except that benzoyl bromide (25 ml) was used instead of pivalic anhydride and no hydrogen chloride in isopropyl alcohol was added. Structure assignment has supported by the nmr spectrum and by elemental analysis.

nmr ((CD₃)₂SO): δ (ppm) 2.12 (s and m, 5H, phenyl CH₃ and pyrrolidine CH₂); 3.13 and 3.59 (pair of m's, each 2H, pyrrolidine CH₂'s); 7.37 (br, 3H, phenyl CH's); 7.4–8.4 (m's, 4H, methylphenyl CH's).

Analysis Calcd. for C₁₈H₁₈N₂O₂.HBr.¼H₂O: C, 56.93; H, 5.18; N, 7.38; Br, 21.04. Found: C, 57.09; H, 4.99; N, 7.32; Br, 20.79.

Example 13

3-[(3,4-dihydro-2H-pyrrol-5-yl)amino]-2-methylphenyl benzoate hydrochloride

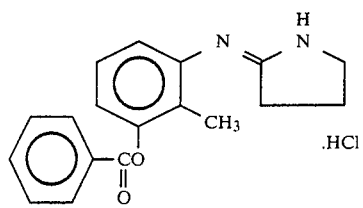

A separate, unrecrystallized preparation of the title product of Example 12 was dissolved in methanol to which was added water. After washing with diethyl ether, the aqueous solution was made basic with aqueous sodium carbonate and extracted with dichloromethane. The organic phase was dried over potassium carbonate, filtered, and concentrated to dryness. The residue was dissolved in methanol and converted to the hydrochloride salt as in Example 10. Structure assignment was supported by elemental analysis; the nmr spectrum was virtually identical to that of the hydrobromide salt (Example 12).

Analysis Calcd. for C₁₈H₁₈N₂O₂.HCl: C, 65.35; H, 5.79; N, 8.47; Cl, 10.72. Found: C, 65.65; H, 5.70; N, 8.41; Cl, 10.98.

Example 14

3-[(3,4-dihydro-2H-pyrrol-5-yl)amino]-2-methylphenyl cyclohexanecarboxylate hydrochloride

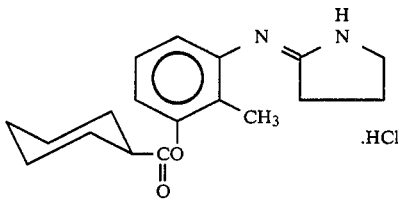

To a mixture of 10 g of the title product of Example 3 and 85 g of cyclohexanecarbonyl chloride was added 0.2 ml of titanium tetrachloride. After heating at 120° for about thirty minutes, the mixture was cooled, washed with ethyl acetate, and decolorized with activated carbon. Recrystallization from methanol-diethyl ether afforded 9.8 g of the title compound. Structure assignment was supported by the nmr spectrum and by elemental analysis.

nmr ((CD₃)₂SO): δ (ppm) 1.0–1.9 (m's, 10H, cyclohexyl CH₂'s); 2.03 (s, 3H, phenyl CH₃); 2.70 (m, 1H, cyclohexyl CH); 2.23, 3.07 and 3.54 (m's, each 2H, pyrrolidine CH₂'s).

Analysis. Calcd. for C₁₈H₂₃N₂O₂.HCl: C, 63.33; H, 7.53; N, 8.20; Cl, 10.39. Found: C, 63.17; H, 7.54; N, 8.21; Cl, 10.69.

Example 15

3-[(3,4-dihydro-2H-pyrrol-5-yl)amino]-2-methylphenyl 2-methoxybenzoate hydrochloride

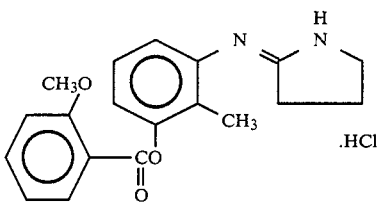

A mixture of 5 g of o-anisic acid and 10 ml of thionyl chloride was heated at 100° for about fifteen minutes. Excess thionyl chloride was removed under reduced pressure to give crude o-anisoyl chloride. The title compound was then prepared from 0.5 g of the title product of Example 3 using the general method of Example 14. Before recrystallization, however, the resultant solid was dissolved in water, made basic with 10% aqueous sodium carbonate, and extracted into dichloromethane. The extract was concentrated to dryness and the residue was purified by column chromatography on silica gel. Fractions containing the free base of the title compound were converted to the hydrochloride as in Example 2. Structure assignment was supported by the nmr spectrum and by elemental analysis.

nmr ((CD₃)₂SO): δ (ppm) 2.13 (s and m, 5H, phenyl CH₃ and pyrrolidine CH₂); 3.09 and 3.55 (pair of m's, each 2H, pyrrolidine CH₂'s); 3.87 (s, 3H, OCH₃).

Analysis Calcd. for C₁₉H₂₀N₂O₃.HCl: C, 63.24; H, 5.87; N, 7.76; Cl, 9.83. Found: C, 63.02; H, 5.81; N, 7.85; Cl, 10.21.

Example 16

3-[(3,4-dihydro-2H-pyrrol-5-yl)amino]-2-methylphenyl acetate hydrochloride

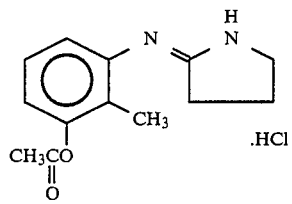

The title compound was prepared from the title product of Example 3 and acetic anhydride using the general method described in Example 10, except that titanium tetrachloride was included as in Example 14. Structure assignment was supported by the nmr spectrum and by elemental analysis.

nmr ((CD₃)₂SO): δ (ppm) 2.1 (s and m, 5H, phenyl CH₃ and pyrrolidine CH₂); 2.32 (s, 3H, acetyl CH₃); 3.08 and 3.53 (pair of m's, each 2H, pyrrolidine CH₂'s); 7.0–7.5 (br, 3H, phenyl CH's).

Analysis Calcd. for C₁₃H₁₆N₂O₂.HCl: C, 58.10; H, 6.38; N, 10.42; Cl, 13.13. Found: C, 57.96; H, 6.42; N, 10.43; Cl, 13.27.

Example 17-24

The following compounds were prepared from the title product of Example 3 (or Example 4) and the appropriate carboxylic acid chloride using the general method described in Example 14. Reaction temperature varied from 120°-150° and additional titanium tetrachloride was sometimes used; some recrystallizations used ethanol in place of methanol. All structure assignments were supported by nmr spectra and by elemental analyses.

Example 17

3-[(3,4-dihydro-2H-pyrrol-5-yl)amino]-2-methylphenyl 4-methoxybenzoate hydrochloride ⅜ hydrate nmr (($CD_3$)$_2$SO): δ (ppm) 2.12 (s and m, 5H, phenyl $CH_3$ and pyrrolidine $CH_2$); 3.06 and 3.57 (pair of m's, each 2H, pyrrolidine $CH_2$'s); 3.87 (s, 3H, $OCH_3$); 7.30 (br, 3H, phenyl CH's); 7.13 and 8.09 (d's, each 2H, methoxyphenyl CH's).

Analysis Calcd. for $C_{19}H_{20}N_2O_3 \cdot HCl \cdot \frac{3}{8}H_2O$: C, 62.85; H, 5.90; N, 7.72; Cl, 9.76. Found: C, 62.57; H, 5.67; N, 7.63; Cl, 10.09.

Example 18

3-[(3,4-dihydro-2H-pyrrol-5-yl)amino]-2-methylphenyl 2-methylbenzoate hydrochloride nmr (($CD_3$)$_2$SO): δ (ppm) 2.1 (s and m, 5H, phenyl $CH_3$ and pyrrolidine $CH_2$); 2.58 (s, 3H, benzoate $CH_3$); 3.09 and 3.56 (pair of m's, each 2H, pyrrolidine $CH_2$'s); 7.33 (br, 3H, phenyl CH's); 7.2-8.2 (m's, 4H, methylphenyl CH's).

Analysis Calcd. for $C_{19}H_{20}N_2O_2 \cdot HCl$: C, 66.18; H, 6.14; N, 8.12; Cl, 10.28. Found: C, 66.30; H, 6.34; N, 8.12; Cl, 10.31.

Example 19

3-[(3,4-dihydro-2H-pyrrol-5-yl)amino]-2-methylphenyl 4-methylbenzoate hydrochloride nmr (($CD_3$)$_2$SO): δ (ppm) 2.1 (s and m, 5H, phenyl $CH_3$ and pyrrolidine $CH_2$); 2.42 (s, 3H, benzoate $CH_3$); 3.05 and 3.57 (pair of m's, each 2H, pyrrolidine $CH_2$'s); 7.30 (br, 3H, phenyl CH's); 7.90 and 8.02 (d's, each 2H, methylphenyl CH's).

Analysis Calcd. for $C_{19}H_{20}N_2O_2 \cdot HCl$: C, 66.18; H, 6.14; N, 8.12; Cl, 10.28. Found: C, 65.99; H, 6.13; N, 8.12; Cl, 10.19.

Example 20

3-[(3,4-dihydro-2H-pyrrol-5-yl)amino]-2-methylphenyl 4-chlorobenzoate hydrochloride ¼ ethanol nmr (($CD_3$)$_2$SO): δ (ppm) 2.12 (s and m, 5H, phenyl $CH_3$ and pyrrolidine $CH_2$); 3.12 and 3.57 (pair of m's, each 2H, pyrrolidine $CH_2$'s); 7.35 (br, 3H, phenyl CH's); 7.68 and 8.15 (d's, each 2H, chlorophenyl CH's)

Analysis Calcd. for $C_{18}H_{17}N_2O_2Cl \cdot HCl \cdot \frac{1}{4}C_2H_5OH$: C, 58.98; H, 4.95; N, 7.44; Cl, 18.81. Found: C, 58.75; H, 5.00; N, 7.34; Cl, 18.60.

Example 21

3-[(3,4-dihydro-2H-pyrrol-5-yl)amino]-2-methylphenyl 3,4-dichlorobenzoate hydrochloride nmr (($CD_3$)$_2$SO): δ (ppm 2.12 (s and m, 5H, phenyl $CH_3$ and pyrrolidine $CH_2$); 3.11 and 3.56 (pair of m's, each 2H, pyrrolidine $CH_2$'s); 7.35 (br, 3H, phenyl CH's); 7.7-8.4 (m's, 3H, dichlorophenyl CH's)

Analysis Calcd. for $C_{18}H_{16}N_2O_2Cl_2 \cdot HCl$: C, 54.09; H, 4.29; N, 7.01; Cl, 26.61. Found: C, 54.00; H, 4.16; N, 6.98; Cl, 26.30.

Example 22

3-[(3,4-dihydro-2H-pyrrol-5-yl)amino]-2-methylphenyl cyclopropanecarboxylate hydrochloride nmr (($CD_3$)$_2$SO): δ (ppm) 0.9-1.3 (m, 4H, cyclopropyl $CH_2$'s); 2.1 (s and m's, 6H, cyclopropyl CH, phenyl $CH_3$, and pyrrolidine $CH_2$); 3.04 and 3.54 (pair of m's, each 2H, pyrrolidine $CH_2$'s); 7.0-7.5 (m, 3H, phenyl CH's)

Analysis Calcd. for $C_{15}H_{18}N_2O_2 \cdot HCl$: C, 61.12; H, 6.50; N, 9.50; Cl, 12.03. Found: C, 61.15; H, 6.45; N, 9.47; Cl, 12.10.

Example 23

3-[(3,4-dihydro-2H-pyrrol-5-yl)amino]-2-methylphenyl adamantane-1-carboxylate hydrochloride ¼ hydrate nmr (($CD_3$)$_2$SO): δ (ppm) 1.7 (s, 6H, adamantane $CH_2$'s); 2.0-2.1 (s's and m's, 14H, adamantane $CH_2$'s and CH's, phenyl $CH_3$, and pyrrolidine $CH_2$); 3.03 and 3.55 (pair of m's, each 2H, pyrrolidine $CH_2$'s); 6.0-7.6 (m, 3H, phenyl CH's).

Analysis Calcd. for $C_{22}H_{28}N_2O_2 \cdot HCl \cdot \frac{1}{4}H_2O$: C, 67.16; H, 7.56; N, 7.12; Cl, 9.01. Found: C, 67.15; H, 7.56; N, 7.04; Cl, 9.24.

Example 24

3-[(3,4-dihydro-2H-pyrrol-5-yl)amino]-2-methylphenyl furan-2-carboxylate hydrochloride ⅛ methanol nmr (($CD_3$)$_2$SO): δ (ppm) 2.1 (s and m, 5H, phenyl $CH_3$ and pyrrolidine $CH_2$); 3.12 and 3.56 (pair of m's, each 2H, pyrrolidine $CH_2$'s); 6.80, 7.60, 8.23 (q, d, m, respectively, each 1H, furan CH's); 7.2-7.5 (m, 3H, phenyl CH's).

Analysis Calcd. for $C_{16}H_{16}N_2O_3 \cdot HCl \cdot \frac{1}{8}CH_3OH$: C, 59.63; H, 5.43; N, 8.63; Cl, 10.92. Found: C, 59.48; H, 5.42; N, 8.68; Cl. 11.30.

Example 25

The following Tables list the results of the Cholera-induced Intestinal Secretion test, supra, for preferred embodiments of this invention as compared with previously known compounds.

Abbreviations: I—inactive at screening doses; N.T.—not tested.

TABLE I

Prior Art Compounds Disclosed in U.S. Pat. No. 3,563,994
Inhibitory Doses (ID$_{50}$'s) (Subcutaneous Route)

| Compound | ID$_{50}$ |
|---|---|
| (structure with $CH_3OC(O)$, $CH_3$, pyrrolidine-N=, .HCl) | 74.0 |
| (structure with $CH_3O$, $CH_3$, pyrrolidine-N=, .HCl) | I |

TABLE I-continued
Prior Art Compounds Disclosed in U.S. Pat. No. 3,563,994
Inhibitory Doses (ID$_{50}$'s) (Subcutaneous Route)

| Compound | ID$_{50}$ |
|---|---|
| 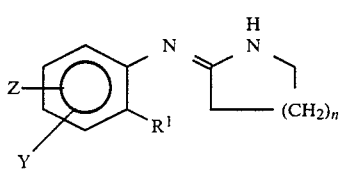 | I |

TABLE II
Preferred Embodiments of This Invention
Inhibitory Doses (ID$_{50}$'s)
(Subcutaneous Route)

| Compound (Example No.) | ID$_{50}$ |
|---|---|
| 3 | 8.3 |
| 5 | 21.3 |
| 6 | 6.5 |
| 10 | 6.4 |
| 11 | 9.0 |
| 12 | 5.7 |
| 14 | 8.1 |
| 15 | 6.2 |
| 16 | 10.1 |
| 17 | 9.5 |
| 18 | 40.5 |
| 19 | 5.9 |
| 20 | 10.6 |
| 21 | 5.0 |
| 22 | 6.8 |
| 23 | 9.1 |
| 24 | 8.3 |

What is claimed is:

1. A compound of the formula:

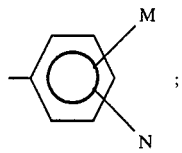

and the pharmaceutically acceptable salts,
wherein Y is OR$^2$;
wherein Z is:
(a) hydrogen;
(b) alkyl of 1 to 6 carbon atoms, inclusive; or
(c) halogen;
wherein R$^1$ is:
(a) hydrogen;
(b) alkyl of 1 to 6 carbon atoms, inclusive; or
(c) halogen;
wherein R$^2$ is:
(a) hydrogen; or
(b) C(=O)R$^3$;
wherein R$^3$ is:
(a) alkyl of 1 to 6 carbon atoms, inclusive;
(b) cycloalkyl of 3 to 8 carbon atoms, inclusive;
(c) multicyclic alkyl of 6 to 12 carbon atoms, inclusive, optionally substituted with one or more alkyl, each of 1 to 6 carbon atoms, inclusive; or
(d)

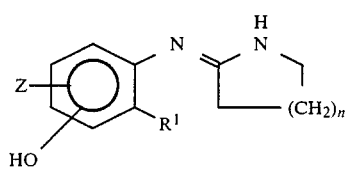

wherein M and N, each being the same or different, are:
(a) hydrogen;
(b) alkyl of 1 to 6 carbon atoms, inclusive;
(c) alkoxy of 1 to 6 carbon atoms, inclusive; or
(d) halogen;
wherein n is 1 or 2.

2. A compound having the formula:

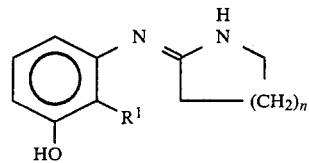

and the pharmaceutically acceptable salts,
wherein Z is:
(a) hydrogen;
(b) alkyl of 1 to 6 carbon atoms, inclusive; or
(c) halogen;
wherein R$^1$ is:
(a) hydrogen;
(b) alkyl of 1 to 6 carbon atoms, inclusive; or
(c) halogen;
wherein n is 1 or 2.

3. A compound having the formula:

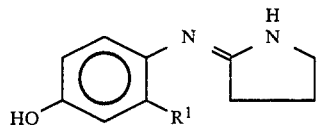

and the pharmaceutically acceptable salts,
wherein R$^1$ is:
(a) hydrogen;
(b) alkyl of 1 to 6 carbon atoms, inclusive; or
(c) halogen;
wherein n is 1 or 2.

4. 3-[(3,4-dihydro-2H-pyrrol-5-yl)amino]phenol, a compound according to claim 3.

5. 3-[(3,4-dihydro-2H-pyrrol-5-yl)amino]-2-methylphenol, a compound according to claim 3.

6. 3-[(3,4,5,6-tetrahydro-2-pyridin-5-yl)amino]-2-methylphenol, a compound according to claim 3.

7. A compound having the formula:

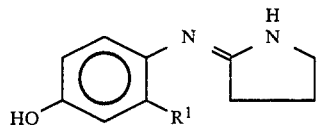

and the pharmaceutically acceptable salts,
wherein R$^1$ is:
(a) hydrogen;
(b) alkyl of 1 to 6 carbon atoms, inclusive; or (c) halogen.

8. 4-[(3,4-dihydro-2H-pyrrol-5-yl)amino]-3-methylphenol, a compound according to claim 7.

9. A compound having the formula:

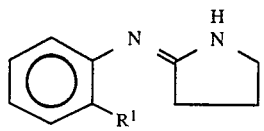

and the pharmaceutically acceptable salts,
wherein $R^1$ is:
(a) hydrogen;
(b) alkyl of 1 to 6 carbon atoms, inclusive; or
(c) halogen.

10. 2-[(3,4-dihydro-2H-pyrrol-5-yl)amino]-3-methylphenol, a compound according to claim 9.

11. A compound having the formula:

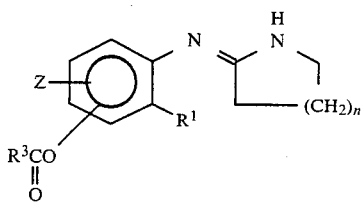

and the pharmaceutically acceptable salts,
wherein Z is:
(a) hydrogen;
(b) alkyl of 1 to 6 carbon atoms, inclusive; or
(c) halogen;
wherein $R^1$ is:
(a) hydrogen;
(b) alkyl of 1 to 6 carbon atoms, inclusive; or
(c) halogen;
wherein $R^3$ is:
(a) alkyl of 1 to 6 carbon atoms, inclusive;
(b) cycloalkyl of 3 to 8 carbon atoms, inclusive;
(c) multicyclic alkyl of 6 to 12 carbon atoms, inclusive, optionally substituted with one or more alkyl, each of 1 to 6 carbon atoms, inclusive; or
(d)

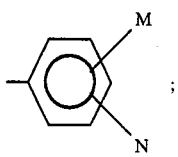

wherein M and N, each being the same or different, are:
(a) hydrogen;
(b) alkyl of 1 to 6 carbon atoms, inclusive;
(c) alkoxy of 1 to 6 carbon atoms, inclusive; or
(d) halogen;
wherein n is 1 or 2.

12. A compound having the formula:

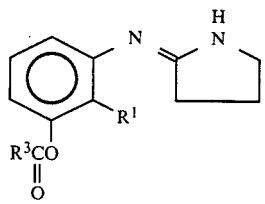

and the pharmaceutically acceptable salts,
wherein $R^1$ is:
(a) hydrogen;
(b) alkyl of 1 to 6 carbon atoms, inclusive; or
(c) halogen;
wherein $R^3$ is:
(a) alkyl of 1 to 6 carbon atoms, inclusive;
(b) cycloalkyl of 3 to 8 carbon atoms, inclusive;
(c) multicyclic alkyl of 6 to 12 carbon atoms, inclusive, optionally substituted with one or more alkyl, each of 1 to 6 carbon atoms, inclusive; or
(d)

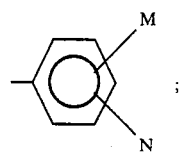

wherein M and N, each being the same or different, are:
(a) hydrogen;
(b) alkyl of 1 to 6 carbon atoms, inclusive;
(c) alkoxy of 1 to 6 carbon atoms, inclusive; or
(d) halogen.

13. A compound having the formula:

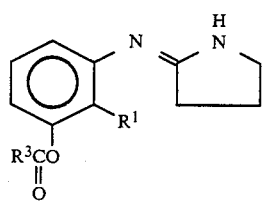

and the pharmaceutically acceptable salts,
wherein $R^1$ is:
(a) hydrogen;
(b) alkyl of 1 to 6 carbon atoms, inclusive; or
(c) halogen;
wherein $R^3$ is alkyl of 1 to 6 carbon atoms, inclusive.

14. 3-[(3,4-dihydro-2H-pyrrol-5-yl)amino]-2-methylphenyl acetate, a compound according to claim 13.

15. 3-[(3,4-dihydro-2H-pyrrol-5-yl)amino]-2-methylphenyl 2,2-dimethylpropanoate, a compound according to claim 13.

16. A compound having the formula:

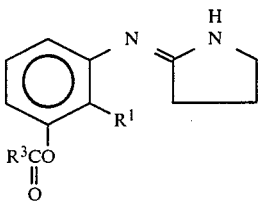

and the pharmaceutically acceptable salts,
  wherein R¹ is:
    (a) hydrogen;
    (b) alkyl of 1 to 6 carbon atoms, inclusive; or
    (c) halogen;
  wherein R³ is cycloalkyl of 3 to 8 carbon atoms, inclusive.

17. 3-[(3,4-dihydro-2H-pyrrol-5-yl)amino]-2-methylphenyl cyclopropanecarboxylate, a compound according to claim 16.

18. 3-[(3,4-dihydro-2H-pyrrol-5-yl)amino]-2-methylphenyl cyclohexanecarboxylate, a compound according to claim 6.

19. A compound having the formula:

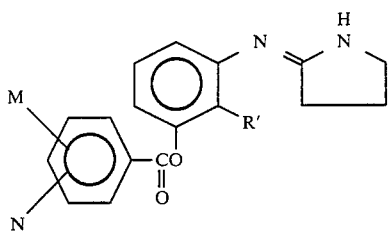

and the pharmaceutically acceptable salts,
  wherein R¹ is:
    (a) hydrogen;
    (b) alkyl of 1 to 6 carbon atoms, inclusive; or
    (c) halogen;
  wherein M and N, each being the same or different, are:
    (a) hydrogen;
    (b) alkyl of 1 to 6 carbon atoms, inclusive;
    (c) alkoxy of 1 to 6 carbon atoms, inclusive; or
    (d) halogen.

20. 3-[(3,4-dihydro-2H-pyrrol-5-yl)amino]-2-methylphenyl benzoate, a compound according to claim 19.

21. 3-[(3,4-dihydro-2H-pyrrol-5-yl)amino]-2-methylphenyl 2-methoxybenzoate, a compound according to claim 19.

22. 3-[(3,4-dihydro-2H-pyrrol-5-yl)amino]-2-methylphenyl 4-methoxybenzoate, a compound according to claim 19.

23. 3-[(3,4-dihydro-2H-pyrrol-5-yl)amino]-2-methylphenyl 2-methylbenzoate, a compound according to claim 19.

24. 3-[(3,4-dihydro-2H-pyrrol-5-yl)amino]-2-methylphenyl 4-methylbenzoate, a compound according to claim 19.

25. 3-[(3,4-dihydro-2H-pyrrol-5-yl)amino]-2-methylphenyl 4-chlorobenzoate, a compound according to claim 19.

26. 3-[(3,4-dihydro-2H-pyrrol-5-yl)amino]-2-methylphenyl 3,4-dichlorobenzoate, a compound according to claim 19.

27. A compound having the formula:

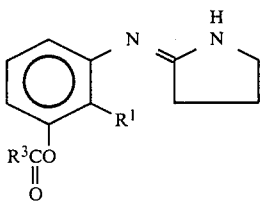

and the pharmaceutically acceptable salts,
  wherein R¹ is:
    (a) hydrogen;
    (b) alkyl of 1 to 6 carbon atoms, inclusive; or
    (c) halogen;
  wherein R³ is multicyclic alkyl of 6 to 12 carbon atoms, inclusive, optionally substituted with one or more alkyl, each of 1 to 6 carbon atoms, inclusive.

28. 3-[3,4-dihydro-2H-pyrrol-5-yl)amino]-2-methylphenyl adamantane-1-carboxylate, a compound according to claim 27.

29. A compound having the formula:

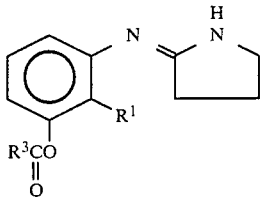

and the pharmaceutically acceptable salts,
  wherein R¹ is:
    (a) hydrogen;
    (b) alkyl of 1 to 6 carbon atoms, inclusive; or
    (c) halogen;
  wherein R³ is:
    (a) alkyl of 1 to 6 carbon atoms, inclusive;
    (b) cycloalkyl of 3 to 8 carbon atoms, inclusive;
    (c) multicyclic alkyl of 6 to 12 carbon atoms, inclusive, optionally substituted with one or more alkyl, each of 1 to 6 carbon atoms, inclusive; or
  (d)

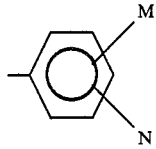

wherein M and N, each being the same or different, are:
    (a) hydrogen;
    (b) alkyl of 1 to 6 carbon atoms, inclusive;
    (c) alkoxy of 1 to 6 carbon atoms, inclusive; or
    (d) halogen.

30. 4-[(3,4-dihydro-2H-pyrrol-5-yl)amino]-3-methylphenyl 2,2-dimethylpropanoate, a compound according to claim 29.

* * * * *